(12) United States Patent
Milbocker et al.

(10) Patent No.: US 11,470,843 B2
(45) Date of Patent: Oct. 18, 2022

(54) TISSUE BONDING INSECT REPELLENT

(71) Applicant: Hour 72, New York, NY (US)

(72) Inventors: Michael Milbocker, Holliston, MA (US); Kenneth O. Rothaus, New York, NY (US)

(73) Assignee: HOUR 72, New York, NY (US)

( * ) Notice: Subject to any disclaimer, the term of this patent is extended or adjusted under 35 U.S.C. 154(b) by 0 days.

(21) Appl. No.: 16/382,671

(22) Filed: Apr. 12, 2019

(65) Prior Publication Data

US 2019/0313636 A1 Oct. 17, 2019

Related U.S. Application Data (60) Provisional application No. 62/659,096, filed on Apr. 17, 2018.

(51) Int. Cl.

| | | |
|---|---|---|
| *A01N 25/10* | (2006.01) | |
| *A01N 37/26* | (2006.01) | |
| *A01N 25/04* | (2006.01) | |
| *A61K 8/87* | (2006.01) | |
| *A61Q 17/02* | (2006.01) | |

(52) U.S. Cl.
CPC ............ *A01N 25/10* (2013.01); *A01N 25/04* (2013.01); *A01N 37/26* (2013.01); *A61K 8/87* (2013.01); *A61Q 17/02* (2013.01)

(58) Field of Classification Search
CPC .......... A61K 8/90; A61K 36/58; A01N 65/00; A01N 25/10; A01N 65/40
See application file for complete search history.

(56) References Cited

U.S. PATENT DOCUMENTS

| | | | |
|---|---|---|---|
| 2,435,005 A | | 1/1948 | Huppke et al. |
| 3,590,188 A | | 6/1971 | Conrady et al. |
| 4,477,467 A | | 10/1984 | Nishizawa et al. |
| 4,756,905 A | | 7/1988 | Melnik |
| 2,356,801 A | | 8/1994 | Travis et al. |
| 5,575,988 A | * | 11/1996 | Knowles, Jr. ............ A61K 8/42 424/59 |
| 5,916,541 A | | 6/1999 | Stewart |
| 2002/0197292 A1 | * | 12/2002 | Fowler ...................... A61K 8/06 424/401 |
| 2005/0054532 A1 | * | 3/2005 | Kocur ..................... A01N 25/10 504/211 |
| 2006/0153891 A1 | | 7/2006 | Gonzalez et al. |
| 2007/0009616 A1 | * | 1/2007 | Marks .................... A01N 65/12 424/745 |
| 2007/0042182 A1 | * | 2/2007 | Markus .................. A01N 65/00 428/402.2 |
| 2010/0260687 A1 | | 10/2010 | Yu et al. |
| 2014/0271503 A1 | | 9/2014 | Milbocker et al. |
| 2016/0184196 A1 | | 6/2016 | Baxter et al. |

* cited by examiner

*Primary Examiner* — Kyle A Purdy (74) *Attorney, Agent, or Firm* — ArentFox Schiff LLP (57) ABSTRACT

The present disclosure generally provides topically applicable insect repelling compositions, and in some embodiments, topically applicable insect repelling and UV protecting compositions. The compositions comprise a polymerization product of a polyol, a diisocyanate and at least one insect-repelling compound. The resulting polymers advantageously bond superficially to skin or hair, thereby localizing repellents and preventing systemic absorption. While not being bound by theory, it is believed that the localization of repellents to the surface of the skin renders them safer, wherein such repellents are not vaporized and do not have a disagreeable odor. The repellents advantageously interact with tactile insect activity, thereby preventing parasitic activity, such as drawing blood or the communication of pathogens.

19 Claims, 2 Drawing Sheets

TISSUE BONDING INSECT REPELLENT

CROSS-REFERENCES TO RELATED APPLICATIONS

This application claims benefit of the U.S. Provisional Application No. 62/659,096, filed on Apr. 17, 2018, which is hereby incorporated by reference in its entirety.

TECHNICAL FIELD

The present disclosure generally provides topically applicable insect repelling compositions, and in some embodiments, topically applicable insect repelling and UV protecting compositions. The compositions comprise a polymerization product of a polyol, a diisocyanate and at least one insect-repelling compound. The resulting polymers advantageously bond superficially to skin or hair, thereby localizing repellents and preventing systemic absorption. While not being bound by theory, it is believed that the localization of repellents to the surface of the skin renders them safer, wherein such repellents are not vaporized and do not have a disagreeable odor. The repellents advantageously interact with tactile insect activity, thereby preventing parasitic activity, such as drawing blood or the communication of pathogens.

BACKGROUND OF THE INVENTION

The present invention relates generally to insect-repelling compositions for topical application to skin and hair. Bites of mosquitoes belonging to the genera *Anopheles* Meigen, *Aedes* Meigen, *Culex* L. and *Haemagogus* L. are a general nuisance and are responsible for the transmission of pernicious tropical diseases, such as malaria, hemorrhagic dengue and yellow fevers and filariasis (elephantiasis). Plants are natural sources of mosquito repelling essential oils (EOs), glyceridic oils and repellent and synergistic chemicals. Plants that have insect repelling EOs include citronella [*Cymbopogon nardus* (L.) Rendle, *C. winterianus* Jowitt ex Bor], eucalyptus (*Eucalyptus* L'Her. spp.), camphor [*Cinnamomum camphora* (L.) J. Presl], cinnamon (*Cinnamomum zeylanicum* Blume), clove [*Syzygium aromaticum* (L.) Men. & L. M. Perry], geranium (*Pelargonium graveolens* L'Her.), lavender (*Lavandula angustifolia* Mill.), lemon [*Citrus x limon* (L.) Osbeck], lemongrass [*Cymbopogon citratus* (DC.) Stapf], peppermint (*Mentha x piperita* L.). Repellent chemicals present in EO compositions or added as pure natural ingredients include geraniol, limonene, p-menthane-3,8-diol, nepetalactone and vanillin. Essential oils have also been used in combination with synthetic insect control agents having mosquito repellent properties such as pyrethroids, N,N-diethyl-m-toluamide (DEET), (±)-p-menthane-3,8-diol (PMD) and dialkyl phthalates. Scientific literature sources provide evidence for the mosquito repellency of many of the EOs and individual chemical components found in EOs.

Many insects, in addition to mosquitos, are classified as pests, and many efforts have been made to eradicate or at least control them. However, although effective poisons have been produced, various insects have developed resistance to them and others have been able to detect and avoid poisons. Furthermore, many poisons have undesirable effects on human and other animal life, and therefore uses thereof have often been regulated or forbidden. In many cases, an effective repellent is preferred to poisons. Similarly, when such repellents are of low toxicity they may be applied to the human body and onto pets, zoo animals and livestock. Some repellents are foul smelling and discoloring, these adverse properties can seriously limit their utilities. Many of the useful insect repellents reported in the literature are-tertiary amides and of these the one heretofore regarded as the most effective all-purpose insect repellent is N,N-diethyl-m-toluamide (DEET).

Desirably, such compounds also would be of improved physical characteristics, such as of even better aroma, non-staining character, even lower toxicity, improved stability, greater substantivity to substrates, and repellency against a broader group of insect types.

In many instances it is more advantageous to repel insect pests from a given place than it is to kill them after they have entered it. Some insect pests inherently are difficult to kill, or the nature of the place where the pests are found may make it undesirable to kill them there. It is considered to be more desirable to repel pests such as mosquitoes and flies from the vicinity of an animal. In a number of instances, such as in the treatment of laborers in the field, it is desirable to use repellents to prevent the movement of insect pests into an area and from one area to another.

Pyrethrins are a class of compounds from blossoms of pyrethrum flowers (*Chrysanthemum cinerariaefolium*) grown mainly in East Africa, containing a cyclopropanecarboxylate group. The pyrethrins are effective as insect repellents, but they are short-lived. The cyclopropanecarboxylate can be modified by hydrolyzation of the ester group to be useful in the present invention.

Although pyrethrins display relatively low toxicity toward mammals and do not leave harmful residues, they undergo rapid biodegradation, they have poor photooxidative stability, their availability is uncertain, and it is costly to extract and process them. Thus, their use has been limited. For a number of years, efforts have been underway around the world to produce synthetic cyclopropanecarboxylate insecticides, pyrethroids, which would overcome these disadvantages. 5-Benzyl-3-furyl methyl chrysanthemate (resmethrin), a powerful contact insecticide, was an early success. A notable recent result of these efforts was the discovery of the pyrethroid, 3-phenoxybenzyl 3-(β-β-dichlorovinyl)-2,2-dimethylcyclopropane carboxylate, having the knockdown attributes of the natural pyrethrins and resmethrin together with a previously unattained level of photooxidative stability.

Lemon *eucalyptus* oil is said to be as effective as DEET (N, N-diethyl-m-toluamide) in insect repellents, and is believed to be recommended by the Center for Disease Control (CDC) and the EPA for use against the mosquitoes known to carry West Nile virus, which causes West Nile fever. Oil of lemon *eucalyptus* is reddish in color and is said to have a menthol-like smell and a coolant like effect. It is apparently used in aromatherapy for relief of congestion, emphysema, and smokers' cough, as Well as for sore throats. It is said to be an antifungal and anti-infectious agent suitable for helping against respiratory and skin infections, and to have anti-inflammatory and insecticidal properties. It can apparently be applied by inhalation, bath, lotion, ointment, diffuser, or a room spray. According to contraindications, lemon *eucalyptus* oil should be diluted prior to applying it on the skin.

Examples of patents relating to insect repellents include U.S. Pat. No. 4,756,905, entitled "INSECT-REPELLENT CAMOUFLAGE COMPOSITION", issued on Jul. 12, 1988 to J. Melnik discloses a composition for repelling insects and camouflaging the human skin. The insect repellent, N,N Diethyl-m-toluamide ("DEET), and a camouflage pigment are combined along with an optional emulsifier to allow a single application to serve both the camouflage and insect repellent functions.

U.S. Pat. No. 3,590,118, entitled "LONG LASTING INSECT REPELLENT FILMS FOR SKIN AND OTHER SUBSTRATES", issued on Jun. 29, 1971 to J. A. Conrady, et al. discloses a long-lasting insect repellent film for skin application. The active chemical agents are dissolved in interpolymer resins to provide a slow release system for the active chemical agents when spread and dried as a film on a human being. The coating can be applied by spraying or spreading and it is alleged to be easily removable with a soapy water solution.

U.S. Pat. No. 2,435,005, entitled "SKIN PROTECTIVE OINTMENT", issued on Jan. 27, 1948 to W. F. Huppke, et al. discloses a cream or ointment containing a film-former So that the cream or ointment forms a film on the wearer's skin. The cream or ointment may include an insect repellent or a sunscreen, or both. Preferably, the film former is a mixture of ethyl cellulose and shellac.

U.S. Pat. No. 4,477,467, entitled "INSECT REPELLENT", issued on Oct. 16, 1984 to K. Nishizawa, et al. discloses the use of DEET in combination with certain proton acceptors for the purpose of inhibiting the absorption of DEET into the wearer's skin.

U.S. Pat. No. 2,356,801, entitled "INSECT REPELLENT COMPOSITION", issued on Aug. 29, 1994 to B. V. Travis, et al. discloses an insect repellent composition in which four insect repellent compounds are combined to improve the effectiveness of the composition.

Nevertheless, there is a need for insect repelling compositions that are long lasting, non-irritating and resist absorption by the skin. The present disclosure addresses these needs. Further, there is a need for a composition that provides both insect repelling and sun-blocking effects for a prolonged period of time, even in the presence of water.

BRIEF SUMMARY OF THE INVENTION

The present invention relates to insect repellents that are chemically bonded to a multi-armed molecule, with at least one arm capable of bonding superficially to skin. The backbone molecule is a poly(ethylene), or poly(propylene) or poly(ethylene)-poly(propylene) copolymer with end groups comprising amine or isocyanate groups. That is, when these multifunctional molecules are reacted with known insect repellent a molecule results that contains these repellents and also retains a skin bonding moiety. For example, a polyalkane with a terminal isocyanate or amine group will readily bond to superficial skin, that is dead skin, and whatever is attached to the molecule is sequestered from permeation into tissue, thereby preventing an immunological response. Furthermore, such a skin localized insect repellent will not have a noticeable odor, but will repel insects based on their landing contact.

Basic starting molecules of the present invention comprise polyalkenes terminated with amines or isocyanate groups. These groups react with the pendent groups of any insect repellents containing amine or hydroxyl groups. Insect repellents not containing these groups usually can be modified to produce a terminal amine or hydroxyl group without losing the insect repellent effectiveness. For example, esters can be converted to alcohols.

For example, an alcohol such as Geraniol is found in roses (with 2-phenylethanol), citronella oil, pomerosa oil, geraniums, and other flowers. A-Terpineol is found in pine oil and juniper; it is used as a perfume and bactericide in many household cleaners. Menthol is found in peppermint and other mint oils. It has a pleasant cooling taste, since it causes the "cold" receptors on the tongue to activate at higher temperatures than normal (such as body temperature). Menthol is used in cough drops, shaving lotion, and mentholated tobacco. In particular, Citronellol, or hydro geraniol, is a natural acyclic monoterpenoid. Both enantiomers occur in nature. (+)-Citronellol, which is found in citronella oils, including *Cymbopogon nardus* (50%), is the more common isomer. (−)-Citronellol is found in the oils of rose (18-55%) and *Pelargonium* geraniums. Or alternatively Eucalyptol, or Azadirachtin, a chemical compound belonging to the limonoid group, is a secondary metabolite present in neem seeds. It is a highly oxidized tetranortriterpenoid which boasts a plethora of oxygen-bearing functional groups, including an enol ether, acetal, hemiacetal, tetra-substituted epoxide and a variety of carboxylic esters.

Synthetic repellents useful in the present compositions include phthalic acid dimethyl ester, 1.2-ethyl hexane 1,3-diol, 3,4-dihydro-2,2-dimethyl-4-oxo-2H-pyran-6-carboxylic acid-n-butyl ester, succinic acid dipropyl ester, N,N-diethyl-3-methyl-benzoic acid amide and pyridine-2,5-dicarboxylic acid-d-n-propyl ester, all of which are useful in the present invention. In some embodiments, molecules of the present invention comprising neoalkanamide groups, which are effective in repelling insects other than mosquitos, such as arachnids, black flies, carpenter ants and deer ticks. In view of the relatively small number of useful insect repellents known, efforts continue to be made to discover additional repellents which would be of greater repellent actions and of longer lasting effects.

Natural insect repellents are obtained from plants by extracting the oils by means of cold expeller pressing, rolling or centrifugation, for example, the essential ingredients are also extracted from the vegetable matter, yielding an oil with superior insect repellent properties. For example, some of the essential ingredients found in Neem oil are various fractions of limonoids, terpenes and terpenoids such as nimbin, salannin, and nimbiol, present in the Azadirachta lndica (Neem) tree and its leaves, bark and seeds. Some of the insect repellent chemicals, which are more numerous in the crude cold pressed oil than in the refined oil, are meliantriol, nimbinin, nimbidin, nimbidol, thionimone, nimatone, nimidol, nimbedic acid, nimbedinic acid, neonimbidin, nimidinin, gedunim, vapinin, meldenin, and vilasinin, as well as certain phyto sterols like beta sitosterol, kaempferol, and some flavonoids such as quercetin and myricetin. Further, Azadirachtin has numerous homologs remaining in the crude pressed oil that do not seem to carry over as well when solvent extracted or heated. They are Azadirone, Azadiradione, beta hydroxy Azadiradione, and delta epi Azadiradione.

By themselves, these bio-chemicals may not have the same bio-activity or insecticidal properties as Azadirachtin, but together they show superior effectiveness as insect repellents. The effectiveness can be further improved by combining the bio-chemicals with other crude cold expeller pressed or ultra-centrifuged essential oils and ingredients that also possess insect repellent properties. In particular, it is most effective to combine Neem oil with Citronella oil and Lemon *Eucalyptus* oil processed in the same manner. The crude cold expeller pressed oil of Citronella contains citral, citronellal, limonene, geraniol, linalool, dipentene and pentinoids. The unrefined oils can be reacted with the base molecule of the present invention, or preferably with purified components of these natural oils.

Other ingredients may be placed on the base molecule to make a protein bonding insect repellent molecule or combined with the protein bonding insect repellent in a mixture to increase the efficacy of the essential oil based molecules. These include thymol or oil of thyme, peppermint oil, menthol, camphor, garlic oil (allyl sulfide), Wintergreen oil (methyl salicylate), oil of pennyroyal (pulegone), oleoresin *capsicum*, and other like substances.

However, taken alone, these substances have minimal effect. Further, thymol may be used more as an antioxidant then to increase the effectiveness of the essential oil composition. UV absorbers or stabilizers may also be added in order to preserve these cold pressed oils against the potential harmful effects of sunlight. Further, the addition of UV absorbers forms a combination sunscreen/insect repellent. Some useful UV absorbers or stabilizers are benzophenones, salicylate esters, cinnamate esters, p-aminobenzoic acid (PABA) esters, and the like.

The fatty alcohols, fatty acid alkyl esters and fatty acids may be obtained by means of a simple chemical reaction from natural or nature-identical, toxicologically harmless raw materials, e.g. by means of hydrolysis, reesterification, hydrogenation, high-pressure hydrogenation, hardening and/or dehydration as known in the prior art. The fatty oils used according to the invention may also be obtained by means of conventional processes from oil-supplying materials such as plant seeds and animal fats. Accordingly, the insect repellent according to the invention contains one or several substances prepared from completely harmless, synthetic (nature-identical) basic substances or directly from natural basic substances, and, consequently, has the least toxicological and irritative risk with an excellent repelling effect. It is preferably used by applying it onto the skin or hair of man and beast to repel flying, biting and sucking insects.

Definitions

The following terms are used herein.

As used herein, the term "synthetic insect repellent" includes without limitation Methyl anthranilate and other anthranilate-based insect repellents, Benzaldehyde, for bees, DEET (N,N-diethyl-m-toluamide), Dimethyl carbate, Dimethyl phthalate, Ethylhexanediol, lcaridin (picaridin), Bayrepel, and KBR 3023, lndalone, a mixture of 60% Dimethyl phthalate, 20% lndalone, 20% Ethyl Hexanediol, IR3535 (3-[N-Butyl-N-acetyl]-aminopropionic acid, ethyl ester), Metofluthrin, Permethrin, SS220, and Tricyclodecenyl allyl ether.

As used herein, the term "natural insect repellent" includes without limitation Beautyberry (*Callicarpa*) leaves, Birch tree bark made into tar and combined with another oil (e.g., fish oil) at ½ dilution, Bog Myrtle (*Myrica Gale*), Catnip oil whose active compound is Nepetalactone Citronella oil, Essential oil of the lemon *eucalyptus* (*Corymbia citriodora*) and its active compound p-menthane-3,8-diol (PMD), Neem oil, Lemongrass, Tea tree oil from the leaves of *Melaleuca alternifolia*, and Tobacco.

BRIEF DESCRIPTION OF THE SEVERAL VIEWS OF THE DRAWINGS

FIG. 1 shows protein bonding isocyanate groups attached to a triol, forming a tissue bonding molecule of the invention.

FIG. 2 shows a tissue bonding molecule of FIG. 1, whereon one of the isocyanate groups has been bonded to citronellol, an insect repellent, to form a protein bonding insect repellent of the invention.

FIG. 3 shows a protein bonding insect repellent of FIG. 2 with one of the protein bonding isocyanate groups bonded to 4-Aminobenzoic acid, a sunscreen, to form a protein bonding insect repellent stabilized with a sunscreen of the present invention.

FIG. 4 is a graph depicting the percentage of mosquitos not landing and biting over a 24-hour period of time using compositions of the present invention compared with 100% DEET.

DETAILED DESCRIPTION OF THE INVENTION

The present insect repellent composition includes one or more insect repellent agent bonded to a skin bonding polymer composition, and anhydrous base. The insect repellent composition can include additional components commonly found in insect repellent compositions including, for example, surfactants, pH adjusting agents, thickeners, emollients, moisturizers, coloring agents, preservatives, antioxidants, chelating agents, UV absorbers and fragrances.

The compositions of the invention may be in any of the forms which are suitable for topical application, in particular in the form of nonaqueous gels, in the form of emulsions obtained by dispersion of a fat phase (also termed the oily phase) in a nonaqueous phase or the reverse, or multiple emulsions. They may be more or less fluid and have the appearance of a white or colored cream, a pomade, a milk, a lotion, a serum, a paste, a powder, a solid stick, and may optionally be packaged as an aerosol and in the form of a foam or spray. These compositions are prepared using the usual methods.

In a particular embodiment of the invention, the composition is in the form of an emulsion and then comprises at least one oily phase. The proportion of the oily phase of the emulsion may be from 1% to 80% by weight, preferably 2% to 50% by weight and more preferably 2% to 40% by weight with respect to the total composition weight. The fats in the oily phase, in particular oils, and the emulsifying and co-emulsifying agents which may be present, used in the composition in the form of an emulsion are selected from those conventionally used in the cosmetics or dermatological field. The emulsifying and co-emulsifying agent, when present, are generally present in a proportion of 0.1% to 30% by weight, preferably 0.3% to 20% by weight and more preferably 0.5% to 15% by weight with respect to the total composition weight. The emulsion may also contain lipid vesicles in addition to or in place of the emulsifying and/or co-emulsifying agents.

The emulsions generally contain at least one emulsifying agent selected from amphoteric, anionic, cationic or non-ionic emulsifying agents used alone or as a mixture. The emulsifying agents are suitably selected as a function of the continuous phase of the emulsion to be produced. When the emulsion is a multiple emulsion, it generally comprises an emulsifying agent in the primary emulsion and an emulsifying agent in the external phase into which the primary emulsion is introduced.

Emulsifying agents which may be used to prepare emulsions which may be cited, are for example alkyl esters or sorbitan ethers, glycerol or sugars; silicone surfactants such as dimethicone copolyols, such as the mixture of cyclomethicone and dimethicone copolyol, marketed under the trademarks DC 5225 C and DC 3225 C by Dow Corning and such as alkyl-dimethicone copolyols such as Lauryl Methicone copolyol marketed under the trademark "Dow Corning 5200 Formulation Aid" by Dow Corning, Cetyl dimethicone copolyol marketed under the trademark Abil EM 90® by Goldschmidt and the mixture of Polyglyceryl-4 isostearate/Cetyl dimethicone copolyol/Hexyl laurate marketed under the trademark Abil WE 09® by Goldschmidt. It is also possible to add thereto one or more co-emulsifying agents which, advantageously, may be selected from the group comprising esters of fatty acids with a branched chain and polyol, in particular esters of fatty acid with a branched chain and glycerol and/or sorbitan and, for example, polyglyceryl isostearate, such as the product marketed under the trademark Isolan GI 34 by Goldschmidt, sorbitan isostearate, such as the product marketed under the trademark Arlacel 987 by ICI, sorbitan isostearate and glycerol, such as the product marketed under the trademark Arlacel 986 by ICI, and mixtures thereof.

Examples of emulsifying agents suitable for the preparation of emulsions which may be cited are nonionic emulsifying agents such as esters of fatty acids and oxyalkylated polyols (more particularly polyoxyethylated), for example polyethylene glycol stearates such as PEG-100 stearate, PEG-50 stearate and PEG-40 stearate; esters of fatty acids and oxyalkylated sorbitan comprising 20 to 100 OE, for example, and for example those marketed under the trademark Tween 20 or Tween 60 by Uniqema; ethers of oxyalkylated (oxyethylenated and/or oxypropylene) fatty alcohols; esters of sugars, alkoxylated or not, such as sucrose stearate and such as PEG-20 methyl glucose sesquistearate; sorbitan esters such as sorbitan palmitate marketed under the trademark Span 40 by Uniqema; esters of a dibasic acid and a fatty alcohol, such as dimyristoyl tartrate; mixtures of these emulsifying agents such as a mixture of glyceryl stearate and PEG-100 stearate (CTFA name: Glyceryl Stearate/PEG-100 Stearate) marketed under the trademark Arlacel 165 by Uniqema and under the trademark SIMULSOL 165 by SEPPIC; or the mixture of dimyristoyl tartrate, cetearyl alcohol, Pareth-7 and PEG-25 laureth-25, marketed under the trademark Cosmacol PSE by Sasol (CTFA name: Dimyristoyl tartrate/cetearyl alcohol/12-15 Pareth 7/PPG 25 laureth 25); mixtures of fatty alcohols and alkyl glycoside, such as the cetearyl alcohol/cetearyl glucoside mixture, for example the commercially available product marketed under the trademark MONTANOV 68 by SEPPIC.

Co-emulsifying agents may be added to said emulsifying agents, such as fatty alcohols containing 8 to 26 carbon atoms, such as cetyl alcohol, stearyl alcohol and a mixture thereof (cetearyl alcohol), octyldodecanol, 2-butyl octanol, 2-hexyldecanol, 2-undecyl pentadecanol or oleic alcohol, or fatty acids, for example.

Examples of oils which can be used in the compositions of the invention are hydrocarbon-containing oils of animal origin such as perhydrosqualene (or squalane); hydrocarbon-containing oils of vegetable origin, such as caprylic/capric acid triglycerides such as those marketed by Stearineries Dubois or those marketed under the trademark Miglyol 810, 812 and 818 by Dynamit Nobel, or oils of vegetable origin, for example sunflower, corn, soya, gourd, grapeseed, sesame, hazelnut, apricot, macadamia nut, arara, coriander, castor, avocado, jojoba oil, shea butter oil; synthesized oils; silicone oils such as volatile or nonvolatile polymethylsiloxanes (PDMS) with a linear or cyclic silicone chain, which are liquid or pasty at ambient temperature; fluorinated oils such as partially hydrocarbonated and/or silicone oils, such as those described in JP-A-2-295912; ethers such as dicaprylyl ether (CTFA name: Dicaprylyl ether); and benzoates of $C_{12}$-$C_{15}$ fatty alcohols (Finsolv TN from FINETEX); arylalkyl benzoate derivatives such as 2-phenylethyl benzoate (X-Tend 226 from ISP); amide oils such as isopropyl N-lauroyl sarcosinate (ELDEW SL-205 from Ajimoto) and mixtures thereof.

The oily phase may also comprise one or more fats selected, for example, from fatty alcohols (cetyl alcohol, stearyl alcohol, cetearyl alcohol), fatty acids (stearic acid) and waxes (paraffin, polyethylene waxes, carnauba, beeswax).

The compositions of the invention may also contain one or more organic solvents which may be selected from the group constituted by hydrophilic organic solvents, lipophilic organic solvents, amphiphilic solvents or mixtures thereof.

Examples of hydrophilic organic solvents which are representative, for example, are linear or branched monohydric alcohols containing 1 to 8 carbon atoms, such as ethanol, propanol, butanol, isopropanol or isobutanol; polyethylene glycols containing 6 to 80 ethylene oxides; polyols such as propylene glycol, isoprene glycol, butylene glycol, glycerol or sorbitol; mono- or di-alkyl isosorbides the alkyl groups of which contain 1 to 5 carbon atoms, such as dimethyl isosorbide; glycol ethers such as diethylene glycol monomethyl or mono-ethyl ether and propylene glycol ethers such as dipropylene glycol methyl ether.

Amphiphilic organic solvents which are exemplary include polypropylene glycol (PPG) derivatives, such as esters of polypropylene glycol and fatty acids, PPG and fatty alcohol such as PPG-23 oleyl ether and PPG-36 oleate.

Examples of lipophilic organic solvents which are exemplary are fatty esters such as diisopropyl adipate, dioctyl adipate or alkyl benzoates.

The compositions of the present invention may also comprise conventional cosmetic adjuvants selected from softeners, moisturizers, opacifying agents, stabilizers, emollients, silicones, anti-foaming agents, fragrances, preservatives, anionic, cationic, nonionic, zwitterionic or amphoteric surfactants, fillers, polymers, propellants, alkalinizing or acidifying agents or any other ingredient which is normally used in the cosmetics and/or dermatological field.

Hydrophilic thickeners which are exemplary include carboxyvinyl polymers such as carbopols (carbomers) and Pemulens (Copolymer acrylate/C1 O-C30-alkylacrylate); cellulose derivatives such as hydroxyethylcellulose; polysaccharides and in particular, gums such as xanthan gum; and mixtures thereof.

Lipophilic thickeners which are exemplary include modified clays, such as hectorite and its derivatives, for example products marketed under the trademark Bentone.

Preservatives which are exemplary include parahydroxybenzoic acid esters also known as Parabens® (in particular methyl paraben, ethyl paraben, propyl paraben), phenoxyethanol, formol liberators such as, for example, imidazolidinyl urea or diazolidinyl urea, chlorhexidine digluconate, sodium benzoate, caprylyl glycol, iodopropynyl butyl carbamate, pentylene glycol, alkyl trimethylammonium bromide such as myristyl-trimethylammonium bromide (CTFA name: Myrtrimonium bromide), dodecyl-trimethylammonium bromide, hexadecyl-trimethylammonium bromide, and mixtures thereof such as the mixture marketed under the trademark Cetrimide® by FEF CHEMICALS. The preservative may be present in the composition of the invention in an amount of 0.001% to 10% by weight with respect to the total composition weight, especially 0.1% to 5% by weight, and in particular 0.2% to 3% by weight.

Examples of fillers which may be included in the compositions of the invention are, for example, pigments; silica powder; talc; polyamide particles, in particular those marketed under the trademark ORGASOL by Atochem; polyethylene powders; powders of natural organic materials such as starch powders, in particular of corn, wheat or rice starch, which may or may not be cross-linked, such as powders of starch cross-linked by octenylsuccinate anhydride, marketed under the trademark DRY-FLO by National Starch; microspheres based on acrylic copolymers, such as those formed from an ethylene glycol dimethacrylate/lauryl methacrylate copolymer marketed by Dow Corning under the trademark POLYTRAP; polymethylmethacrylate powders such as those marketed under the trademark MICROPEARL M 100 by Matsumoto; expanded powders such as hollow microspheres, in particular microspheres marketed under the trademark EXPANCEL by Kemanord Plast or under the trademark MICROPEARL F 80 ED by Matsumoto; silicone resin microbeads, such as those marketed under the trademark TOSPEARL by Toshiba Silicone; polyurethane powders, such as hexamethylene diisocyanate/trimethylol hexyllactone copolymer marketed under the trademark Plastic Powder D-400 by Toshiba Pigment (CTFA name: HD1/ Trimethylol Hexyllactone Crosspolymer); and mixtures thereof. When they are present, these fillers may be in quantities of 0.001% to 20% by weight, preferably 0.1% to 10% by weight and more preferably 1% to 5% by weight with respect to the total composition weight.

The compositions of the invention may constitute a skin care products, or a veterinary products.

Skin Bonding Polymer Component

The insect repellent composition includes a skin bonding polymer component. The skin bonding polymer component can include any polymer that, when applied to the skin, helps hold the insect repellent agent to the skin. The skin bonding polymer component holds the insect repellent agent in proximity to skin tissue when applied to the skin tissue so that the insect repellent agent can protect the skin tissue from biting insects. The skin bonding polymer component can be referred to as the polymer component. The polymer component can be provided as a polymer having an average molecular weight of at least about 2,000. The polymer component can be provided as a polymer having an average molecular weight of less than about 500,000.

The present invention also relates to clothing articles and the like that have the present molecule bonded to them, wherein the coatings include biocompatible polymers based on an aryl group attached to an aromatic ring. More specifically, the present invention relates to clothing articles having coatings, which include multiple insect repellent groups on one molecule.

Chemical compounds of the present invention comprise aromatic ring stabilized insect repellent moiety. The insect repelling compounds can be compounds with pendant hydroxyl (OH) or amine (NH) moieties that react with pendant isocyanate groups of the polymer to form urethane or urea links, to form a protein bonding molecule containing at least one free NCO. The polymeric backbone is preferably multifunctional (multi-armed) and capable of concentrating multiple insect repellent and protein bonding moieties singly or in combination, on a single molecule. Additionally, one or more of the polymeric backbone arms may be substituted with a protein bonding or clothing article bonding moiety.

Figure 1:
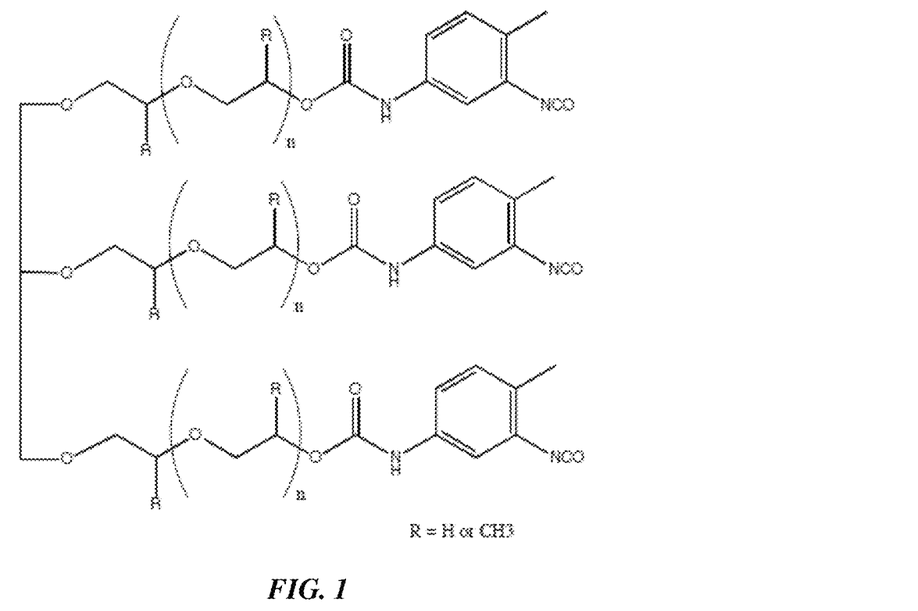

In addition to its functional aspects, the polymeric backbone provides shielding benefits to the insect repellent groups, preventing them from degradation due to the presence of water. The polymer chain comprises hydrophilic groups and hydrophobic groups. The hydrophilic groups are positioned such that the overall insect repellent molecule is biocompatible and does not cause an allergic response which may degrade or otherwise render less functional the insect repellent molecule. The hydrophobic groups are positioned such that water is repelled from the aromatic ring structure comprising the protein bonding or insect repellent groups. Clearly, the degree of hydrophobic shielding can be adjusted by the position, size and distribution of hydrophobic and hydrophilic segments on the polymer backbone R1. The intervening aromatic ring structure, positioned between the polymeric backbone R 1 and the insect repellent moiety R2, balances the insect repellent or protein bonding group with an opposing urethane or urea group connecting the polymeric backbone to the aromatic ring.

Due to the resonant structure of aromatic rings, the effect of the opposing urethane or urea group tends to increase positive charge in the vicinity of the insect repellent functional group, and consequently tends to increase the stability of such moieties against photodegradation and hydrolysis.

The mechanism of this rate retardation may be attributable simply to repulsive electrostatic interactions, which inhibit attack of positively charged H ions on the insect repellent functional group and slows the rate of its H-catalyzed decomposition.

The invention described herein provides novel insect repellent ether-urethane/urea-aromatic-based polymers ("EUA polymers"). The polymers of the invention preferably comprise at least two insect repellent units and contain at least one aromatic ring associated with each insect repellent unit.

In addition, although less preferred, the present invention can embody other protective moieties in the insect repellent position, including UV absorptive compounds containing pendant hydroxyl or amine groups. Alternatively, these EUA-molecules can be used in a cosmetic mode.

Some embodiments of the present invention are coatings for clothing articles, living area screens, and the like made from one or more of the bonding tissue repellent molecule of the present invention. These insect repellent articles and coatings made in accordance with the teachings of the present invention include embodiments wherein one or more additional bioactive agent is attached to one of the arms of the polymeric backbone. The bioactive agent can be released at the skin surface or function as an interface between the insect repellent and an article or tissue. Preferably, said interface is a covalent bond.

Suitable bioactive agents include, but are not limited to, FKBP12 binding compounds such as Zotarolimus, estrogens, chaperone inhibitors, protease inhibitors, protein-tyrosine kinase inhibitors, leptomycin B, peroxisome proliferator-activated receptor gamma ligands (PPARgamma.), hypothemycin, bisphosphonates, epidermal growth factor inhibitors, antibodies, proteasome inhibitors, antibiotics, anti-inflammatories, antisense nucleotides and transforming nucleic acids.

Alternatively, the EUA-based polymers of the present invention may be delivered as individual molecules with all their functional arms occupied with one or more insect repellent groups wherein the insect repellent polymer is eluted from a substrate polymer in a predetermined fashion. Exemplary embodiments of a delivery device scenario include, but are not limited to, insect-repellent eluting plastics or monofilaments.

When the isocyanate is attached to an aromatic ring, such as is the case of the aromatic isocyanates (e.g. toluene diisocyanate), the reaction with a polyol creates a polyisocyanate. None of the polyisocyanates of the present invention are available commercially, and must be synthesized according to embodiments herein given. The object to be recognized is the bonding of aromatic isocyanates to hydrophilic/hydrophobic polyols as herein described create protein bonding molecules, and in particular, skin and hair bonding molecules. An exemplary three-armed polymer containing three pendant isocyanate groups is depicted in FIG. 1. In this embodiment, the polymer comprises a polyol, wherein n is independently for each occurrence in an integer ranging from 10 to 10,000. In some embodiments, the polyol is a polyethylene oxide, polypropylene oxide or a mixture thereof (i.e., R is independently for each occurrence H or $CH_3$).

Figure 2:
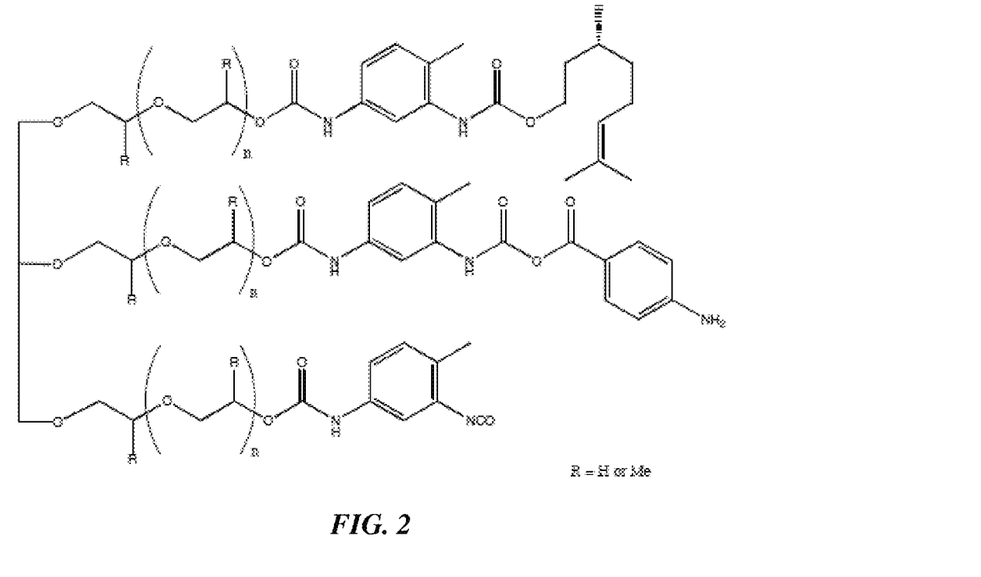

In an embodiment, the polyisocyanate is modified by reacting one of the pendant isocyanate groups with the hydroxyl or amine pendant groups of an insect repelling compound. For example, as depicted in FIG. 2, citonellol can be reacted with a pendant isocyanate group to form an urethane linkage between the citronellol and the polymer backbone.

Figure 3:
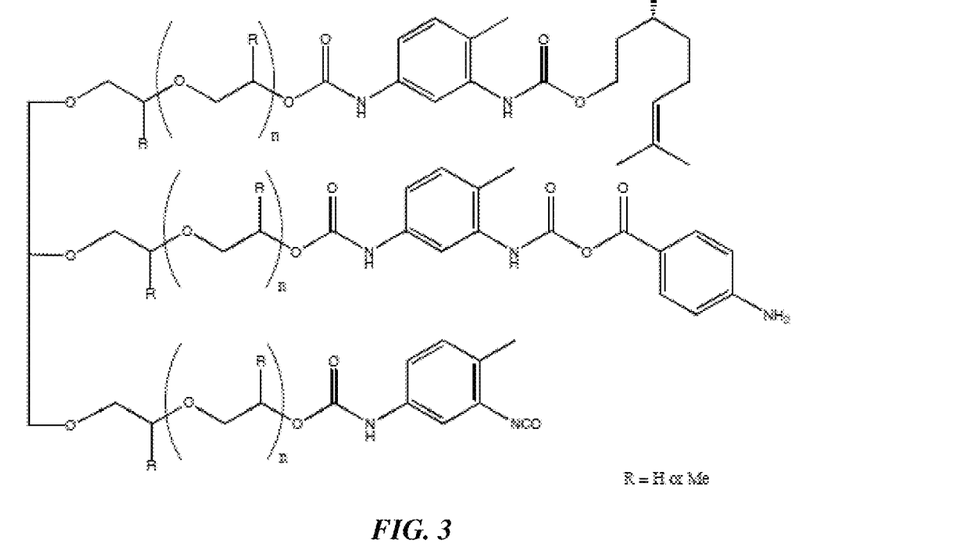

The resulting compound may be further modified by reacting one of the pendant isocyanate groups with the hydroxyl or amine pendant groups of a UV absorber, thereby producing a compound that has both insect repelling and sun-protecting properties. For example, as depicted in FIG. 3, aminobenzoic acid is reacted with a pendant isocyanate group to form a urethane linkage between the aminobenzoic acid and the polymer backbone. This molecule illustrates a protein bonding pendant NCO, an insect repellent group of citronellol, and a UV absorptive group of aminobenzoic acid. These compounds are unusual in having three urethane or urea linkages between the backbone polymer and the diisocyanate, and a urethane or urea linkages between the protein bonding molecule and insect repellent and UV absorptive moieties.

More generally, when the diisocyanate is reacted with an alcohol, such as polyethylene glycol, polypropylene glycol or combinations of these ethers, in sufficient quantities that free NCO groups are pendant, then the diisocyanate forms a urethane or urea link (if the glycol is aminated) between the glycol and the aromatic ring of the diisocyanate. The free NCO group can then participate in urea or urethane link formation when exposed to insect repellent moieties.

The alcohol in this structure is a nucleophile, and bends towards electronegativity of the oxygen, which is substantially greater than that of carbon and hydrogen. Consequently, the covalent bonds of this functional group are polarized so that oxygen is electron rich and both carbon and hydrogen are electrophilic, and the insect repellent group is partially shielded from environmental water.

The aromaticity of the benzene ring between insect repellent moiety and ether moiety stabilizes the insect repellent moiety. The aromatic ring is a conjugated ring of unsaturated bonds, lone pairs, or empty orbitals exhibit a stabilization stronger than would be expected by the stabilization of conjugation alone.

Aromaticity can also be considered a manifestation of cyclic delocalization and of resonance. This is usually considered to be because electrons are free to cycle around circular arrangements of atoms which are alternately single and double-bonded to one another. These bonds may be seen as a hybrid of a single bond and a double bond, each bond in the ring identical to every other. The model for benzene consists of two resonance forms, which corresponds to the double and single bonds superimposing to give rise to six one-and-a-half bonds. Benzene is a more stable molecule than would be expected without accounting for charge delocalization.

One skilled in the art will also recognize the theoretical possibility that some insect repellent moieties can be sequestered in these polymers by electrostatic interaction with the pi electrons contained in the multiple bonds (i.e., to form clathrate-type or sandwich-like structures). Indeed, to some extent, these and other possible structures may exist in the materials of the present invention.

The diisocyanate depicted in FIGS. 1 to 3 is 2,4-toluene diisocyanate, though other diisocyanates may be used. The incorporation of a multi-armed polymer increases the capacity of a molecule to deliver insect repellent moieties and contributes to the stability of the molecule. The combination of increased stability and capacity to deliver insect repellent moieties results in a high insect repellent potency.

A further advantage of these polymers is that they lack the brittleness of other insect repellent compositions and have sufficient elasticity to coat and adhere under physiological conditions to clothing articles, such as caps, shirts, or trousers.

The polymers of the present invention can be prepared from polymers having a multiplicity of nucleophilic groups. Suitable nucleophilic groups include amines, thiols, hydroxyls, hydroxylamines, hydrazines, amides, guanadines, imines, aromatic rings and nucleophilic carbon atoms.

In particular, the polymer may be a triol of ethylene oxide and propylene oxide units distributed so as to render the entire polymeric backbone structure biocompatible. For example, the triol may consist of a copolymer consisting of 25% propylene oxide units and 75% ethylene oxide units, or their glycols, in a block copolymer structure.

Alternatively, diols of ethylene oxide and propylene oxide or copolymers of these can be grafted to a small trifunctional center Such as trimethylolpropane through urethane links. In some cases an absorbable polymer backbone is desired. Typical absorbable, biocompatible links are ester, polysaccharide, or caprolactone moieties. For example, a lactide can be grafted in between the ether units to provide degradation by hydrolysis.

Accordingly, the present invention provides a method of positioning insect repellent structures on a multi-functional base polymer, preferably a polymer of the present invention provides insect protection over a period of at least one day (i.e., at least about 24 hours), more preferably at least three days (i.e., at least about 72 hours), more preferably at least 1 week, and most preferably at least 1 month. In many cases, the stability of the bonding substrate determines the effective duration. For example, the top layer of cells comprising skin normally sloughs off with 50% of the skin area within three days. However, if the bonding substrate is a clothing article, the insect repellent efficacy may last for months. The primary advantage of the present invention is that normally volatile compounds are covalently bonded to a more durable substrate.

Additionally, there is a further benefit, in that many of the volatile insect repellent compounds of the present invention are rendered non-volatile, that is they cannot be detected by smell. Essential oils repellent to insects tend to have strong odors which may be offensive. The present invention eliminates the formation of ambient odors, which is also characteristic of their durability and longevity regarding efficacy.

In another embodiment, the polymeric backbone can have a star structure. For example, the triol can be further polymerized by three triols, one attached to each are of the central triol to create a star configuration comprising 6 arms, each terminated with a hydroxyl group. This star structure then acts as the base polymer. The multifunctional aspect of the base polymer can serve to provide compounds that have a multiphasic functionality. While the ring stabilized form of the insect repellent structures of the present invention have much extended residence times compared to non-polymerized essential oils, these ring stabilized structures can localize free forms of the essential oils. That is, a few protein bonding molecules can serve as localizing centers for free insect repellent moieties.

Another embodiment provides insect repellent clothing articles and a clothing article comprising polymers, wherein the polymers and co-polymers possess a functional isocyanate group on one of the base polymer arms. Such isocyanates are capable of bonding to other molecules with an amine or hydroxyl functionality. More specifically, the present invention relates to clothing articles and clothing article coatings having which include insect repellent, biocompatible, biodegradable polymers and co-polymers.

Thus the present invention provides at least two was for enhancing an insect repellent molecule biocompatibility. In one embodiment of the present invention the biocompatible, biodegradable, insect repellent polymers and copolymers made in accordance with the teachings of the present invention are used to provide coatings for clothing articles. The coating may or may not include an additional bioactive agent on one of the arms. For example, one arm of a polymer triol structure contains a UV absorptive group, another arm contains an isocyanate groups, and a third arm contains an insect repellent group.

In another embodiment of the present invention the entire clothing article is made using the biocompatible insect repellent polymers and copolymers made in accordance with the teachings of the present invention.

Clothing articles made in accordance with the teachings of the present invention include, but are not limited to, screens, masks, undergarments, trousers, protective wear, gloves, facial covering, footwear, both functional and cosmetic.

The compounds and compositions of the invention are useful for treating an animal, e.g., a mammal such as a human, for infestation with, for example, a lice, a tick, or generally a parasite. The method comprises administering topically to the animal, e.g., human, an amount of a compound of the invention or composition thereof sufficient to treat the infestation in the animal.

The following examples are meant to be illustrative, and not limiting.

Example 1

Synthesis of Polymer backbone: A poloxamer triol, such as dry (<300 ppm H2O) Multranol 3901 (Bayer, Morristown, N.J.) containing 1 mole of hydroxyl groups, is combined with toluene diisocyanate containing 2 moles of NCO groups in a glass reactor equipped with a stirrer, heating jacket and temperature sensor. The reactor is purged with dry nitrogen and the mixture stirred. The reaction volume is heated to 40° C. and allowed to react until the exotherm has subsided. Then the temperature of the reactor is increased in 5° C. increments, stopping after each increment to let the exotherm subside, until a temperature of 65° C. is reached. The reaction mixture is further reacted until 1 mole of isocyanate group is consumed. This endpoint can be determined by measuring the % NCO.

Example 2

An insect repellent Polymer: The polymer backbone of Example 1 is placed in a reactor. The reactor is purged with dry nitrogen. The volume is stirred and an insect repellent molecule is delivered to the reaction volume. The polymer will immediately begin to react with the introduced insect repellent moiety. A solvent may be used in cases where the polymer base or addition of insect repellent is too viscous.

For example, acetone can be used, and the solvent later removed by vacuum. Alternatively, an inert solvent such as propylene carbonate may be used. The reaction is continued for approximately 12 hours at room temperature, in less time at elevated temperature. The reaction is complete when the residual NCO functionality is the original molar content.

Here, the protein bonding functionality can be adjusted to a particular application. For example, a protein bonding base of Example 1 comprising 3 moles of NCO functionality, can be reacted with an insect repellent comprising one hydroxyl group per molecule in a ratio of 1 mole of Example 1 to 1 mole of insect repellent to yield polymers on average that have two protein bonding arms per molecule. On the other hand if 2 moles of insect repellent are introduced into the reaction, then the resulting molecules will have on average 1 arm that is protein bonding. One can add 1 mole of one insect repellent moiety and another mole of insect repellent moiety to provide hybrid molecules.

Clearly, separate reactions can be performed where one insect repellent molecule is formed, and another different insect repellent molecule is formed, and the two combined. Furthermore, molecules comprising two arms of insect repellent can be combined with molecules of Example 1 to increase protein bonding.

Example 3

A Topical Bonding Insect Repellent: The insect repellent polymer of Example 2 is mixed in an inert base with pleasing cosmetic attributes. The principal requirement for long shelf-life is that the base mixture possess the lowest practical water content, typically less than 300 ppm H2O. For example, a mixture of butylene glycol, sodium lauroyl lactylate, propylene glycol, poloxamer 407 and laureth-4 result in a foaming composition suitable for delivering the insect repellent polymer of Example 2 as a shower wash.

Effective concentrations of insect repellent polymer in topical compositions is generally between 10% and 50%.

Example 4

An Insect repellent Polymer with Tissue/Prosthetic Bonding Functionality: The polymer backbone of Example 1 is placed in a reactor. The reactor is purged with dry nitrogen. The volume is stirred and insect repellent moiety is delivered to the reaction volume. The polymer base will immediately begin to react with the introduced OH or NH groups of the insect repellent. Viscosity will in most cases increase rapidly. A solvent may be used in cases where the polymer base is too viscous. For example, acetone can be used, and the solvent later removed by vacuum. Alternatively, an inert solvent such as propylene carbonate may be used. The reaction is continued until approximately ⅔ of the NCO functionality is consumed. Clearly, any degree of tissue bonding functionality can be obtained by controlling the amount of NCO functionality that is consumed, typically greater than ⅓ of the NCO functionality and less than approximately ⅚ of the NCO functionality.

Example 5

A Clothing Article Coated with an Insect Repellent Polymer: A prosthetic is coated with a solution of insect repellent polymer of Example 2. The insect repellent polymer may be diluted with a volatile solvent such as toluene or acetone. The coated clothing article is then allowed to cure partially in a humid environment. While the coating is still in a fluid state, the coated clothing article is then transferred to a closed box that has been purged with dry nitrogen. The box is filled gaseous NO and the coated prosthetic allowed to react with the NO until all isocyanate functionality is consumed.

Example 6

Figure 4:
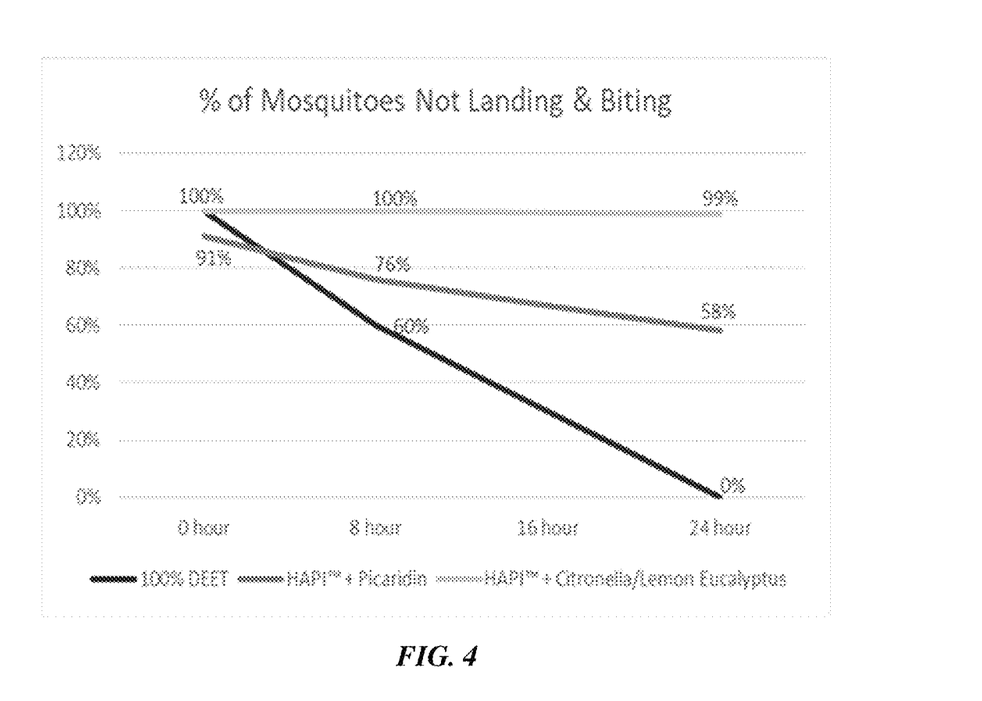

Test of an Insect Repellent Composition: A polymer backbone composition of Example 1 is procured comprising 3 moles of NCO functionality (this polymer is referred to as HAPI in FIG. 4). To this composition is reacted, as described in Example 2, 0.9 moles of OH comprising alcohols of citronella essential oil extract, and 0.9 moles of OH comprising alcohols of lemon *eucalyptus* essential oil extract, and 0.2 moles of OH comprising alcohols of neem essential oil extract. This polymer was compared to a polymer comprising picaridin, and to 100% DEET over a 24-hour period of time. As seen in FIG. 4, the HAPI+cintronella/lemon *eucalyptus* composition had superior repelling activity over a longer period of time.

In summary, the materials and functions of the device of the invention include the following: In one aspect of the invention, an insect repellent polymer comprises: a) a biocompatible base polymer, b) at least one aromatic ring, and c) an insect repellent group. The biocompatible base polymer is attached to the aromatic ring through a urethane or urea link at one position on the aromatic ring, and the insect repellent group is attached at another site on the same aromatic ring or on an additional aromatic ring. The biocompatible base polymer is multifunctional, and may be a poloxamer triol comprised of polypropylene and polyethylene segments. The insect repellent polymer may be made by reacting a multi-functional alcohol with a diisocyanate until all hydroxyl functionality is consumed to provide a macro multi-isocyanate, and by reacting said macro multi-isocyanate with insect repellent until some fraction of isocyanate functionality is consumed.

The insect repellent polymer may be used as a cosmetic base. It may also comprise an insect repellent polymer with bonding functionality comprising: a) a biocompatible base polymer, b) at least one aromatic ring with pendant isocyanate functionality, and c) an insect repellent group, wherein the biocompatible base polymer is attached to the aromatic ring through a urethane or urea link at one position on the aromatic ring and the insect repellent group attached at another site on the same or additional aromatic ring, and an isocyanate group at one or more locations on one or more aromatic rings.

A clothing article may be coated with an insect repellent polymer. The polymer may include a UV absorptive group attached to isocyanate groups that are further reacted with a bioactive molecule.

A method of synthesizing an insect repellent polymer with bonding functionality may comprise the steps of: a) reacting a multi-functional alcohol with a diisocyanate until all hydroxyl functionality is consumed to provide a macro multi-isocyanate, and b) said macro multi-isocyanate reacted with insect repellent OH or NH groups until a portion of isocyanate functionality is consumed.

A method of coating a clothing article with an insect repellent polymer may comprise the steps of: a) coating the clothing article with the polymer; b) partially polymerizing the polymer on the clothing article; and c) further reacting any remaining isocyanate groups with additional insect repellent moieties.

The nitric oxide releasing polymer of the invention is suitable for treatment of a human, or for the coating of a clothing article, for example by the reaction of an insect repellent polymer with a bioactive molecule to coat a clothing article. It is also useful for coating a clothing article, directly or by coating the clothing article with a bioactive molecule, or with an insect repellent polymer, and/or with a cosmetic base.

Thus, although there have been described particular embodiments of the present invention of a new and useful TISSUE BONDING INSECT REPELLENT it is not intended that such references be construed as limitations upon the scope of this invention except as set forth in the following claims.

What is claimed is:

1. A topical insect repellent composition, comprising:
   i) a poloxamer triol bound to at least one insect-repellent molecule via polymerization of a diisocyanate, and
   ii) a carrier suitable for application to the skin or hair;
   wherein the poloxamer triol is a polymerization product of a triol, the diisocyanate, and a poloxamer, such that the product is a polyol comprising 3 arms of poloxamer bonded to one triol;
   wherein the triol is trimethylolpropane or glycerol; and
   wherein the insect-repellent molecule is a compound extractable from a natural oil selected from the group consisting of neem oil, citronella oil, and lemon *eucalyptus* oil.

2. The composition of claim 1, wherein the poloxamer triol is comprised of a block copolymer containing 10 to 60 carbon atoms per block.

3. The composition of claim 1, wherein the composition comprises an NCO weight fraction of less than 20% of the total weight.

4. The composition of claim 1, wherein the poloxamer triol is a multi-armed polymer, wherein at least one arm comprises a terminal NCO group, and at least two other arms are each bound to an insect-repellent molecule.

5. The composition of claim 4, wherein the multi-armed poloxamer triol is a three-armed polymer.

6. The composition of claim 1, wherein the poloxamer triol has a molecular weight between 1,000 and 20,000 Daltons.

7. The composition of claim 4, wherein at least one arm of the poloxamer triol comprises at least one terminal NCO group capable of bonding to human skin.

8. The composition of claim 7 wherein the poloxamer triol is capable of bonding to skin via a covalent bond formed between the terminal NCO group and the skin.

9. The composition of claim 1, wherein the poloxamer triol is further bound to an ultraviolet-absorbing compound.

10. The composition of claim 1 wherein the carrier comprises a free insect repellent and a skin emollient.

11. The composition of claim 10, wherein the free insect repellent is selected from the group consisting of i) a synthetic insect repellent, ii) a natural insect repellent and iii) combinations thereof.

12. The composition of claim 11, wherein the synthetic insect repellent comprises DEET.

13. A topical insect-repellent composition, comprising:
   a compound comprising an insect-repellent molecule bound to a poloxamer triol, wherein the molecular weight of the compound is 500 Daltons or greater, wherein the insect-repellent molecule is a compound extractable from a natural oil selected from the group consisting of neem oil, citronella oil, and lemon *eucalyptus* oil.

14. The composition of claim 13, wherein the insect-repellent molecule is p-menthane-3,8-diol.

15. The composition of claim 13, wherein the poloxamer triol further comprises at least one free isocyanate group.

16. The composition of claim 13, wherein the insect-repellent molecule is picaridin.

17. The topical insect repellant composition of claim 13, wherein the poloxamer triol is a polymerization product of: a triol selected from trimethylolpropane or glycerol, a diisocyanate, and a poloxamer.

18. The composition of claim 1, wherein the insect-repellent molecule is a compound extracted from a natural oil selected from the group consisting of neem oil, citronella oil, and lemon *eucalyptus* oil.

19. The composition of claim 13, wherein the insect-repellent molecule is a compound extracted from a natural oil selected from the group consisting of neem oil, citronella oil, and lemon *eucalyptus* oil.

* * * * *

UNITED STATES PATENT AND TRADEMARK OFFICE
CERTIFICATE OF CORRECTION

| | |
|---|---|
| PATENT NO. | : 11,470,843 B2 |
| APPLICATION NO. | : 16/382671 |
| DATED | : October 18, 2022 |
| INVENTOR(S) | : Michael Milbocker |

It is certified that error appears in the above-identified patent and that said Letters Patent is hereby corrected as shown below:

On the Title Page

Item (72) Inventors read:
Michael Milbocker, Holliston, MA (US);
Kenneth O. Rothaus, New York, NY (US)

Should read:
Michael Milbocker, Holliston, MA (US);
Kenneth O. Rothaus, New York, NY (US);
Andrew Rothaus, Larchmont, NY (US)

Signed and Sealed this
Ninth Day of May, 2023

Katherine Kelly Vidal
*Director of the United States Patent and Trademark Office*